United States Patent [19]

Hutt, Jr. et al.

[11] Patent Number: 4,968,799

[45] Date of Patent: Nov. 6, 1990

[54] ANTIBACTERIAL AGENTS

[75] Inventors: Marland P. Hutt, Jr., Saline; John S. Kiely, Ann Arbor, both of Mich.

[73] Assignee: Warner-Lambert Company, Morris Plains, N.J.

[21] Appl. No.: 452,180

[22] Filed: Dec. 18, 1989

Related U.S. Application Data

[62] Division of Ser. No. 80,113, Jul. 31, 1987, Pat. No. 4,923,879.

[51] Int. Cl.$^5$ .................. C07D 241/04; C07D 471/02
[52] U.S. Cl. ..................................... 544/358; 546/122
[58] Field of Search ...................... 546/122; 544/358

[56] References Cited

U.S. PATENT DOCUMENTS

| | | | |
|---|---|---|---|
| 4,273,778 | 6/1981 | Hadley et al. | 546/122 |
| 4,571,396 | 2/1986 | Hutt et al. | 546/122 |

FOREIGN PATENT DOCUMENTS

| | | | |
|---|---|---|---|
| 0215650 | 3/1987 | European Pat. Off. | 546/122 |
| 3601567 | 7/1987 | Fed. Rep. of Germany | 546/122 |
| 3632222 | 4/1988 | Fed. Rep. of Germany | 546/122 |

*Primary Examiner*—Mary C. Lee
*Assistant Examiner*—J. Richter
*Attorney, Agent, or Firm*—Elizabeth M. Anderson

[57] ABSTRACT

Novel quinoline-, naphthyridine-, and benzoxazine-carboxylic acid derivatives with bridged sidechains useful as antibacterial agents are described. Methods for their preparation, formulation, and use in treatment of bacterial infections is also described.

2 Claims, No Drawings

ANTIBACTERIAL AGENTS

This is a divisional of U.S. patent application Ser. No. 080,113 filed July 31, 1987, now U.S Pat. No. 4,923,879.

BACKGROUND OF THE INVENTION

U.S. Pat. No. 4,571,396 discloses certain naphthyridine-, quinoline-, and benzoxazinecarboxylic acids containing bridged sidechains. The compounds are disclosed as having antibacterial activity in vitro.

SUMMARY OF THE INVENTION

One aspect of the present invention is a compound of the formula

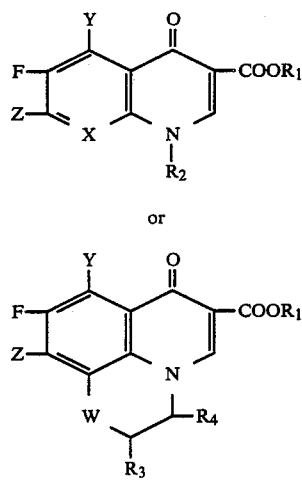

wherein Z is

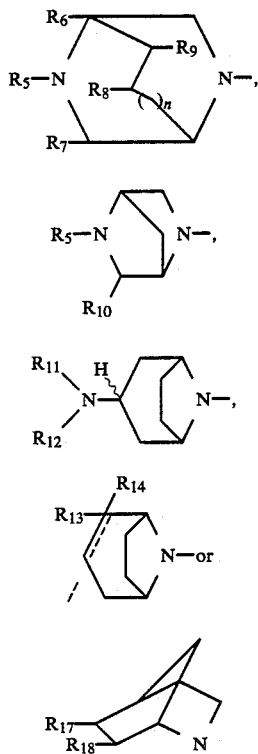

wherein n is 0 or 1;

$R_5$ and $R_6$ are each independently hydrogen, methyl, ethyl, or benzyl with the proviso that if $R_6$ is hydrogen, n cannot be 0;

$R_7$, $R_8$, and $R_9$ are each independently hydrogen or methyl, with the proviso that if $R_6$ is hydrogen, $R_8$ and $R_9$ cannot both be hydrogen;

$R_{10}$ is methyl, ethyl or isopropyl;

$R_{11}$ and $R_{12}$ are each independently hydrogen, alkyl of from one to three carbon atoms, isopropyl or cyclopropyl with the proviso that both $R_{11}$ and $R_{12}$ cannot both be hydrogen;

the dotted line means a single or double bond;

$R_{13}$ is $CH_2OR_{15}$, $CH_2NR_{15}R_{16}$, or $NR_{15}R_{16}$ wherein $R_{15}$ and $R_{16}$ are hydrogen, alkyl of from 1-3 carbons, acyl of from 1-3 carbons; $R_{14}$ is hydrogen or alkyl of 1-3 carbons;

$R_{17}$ and $R_{18}$ are each independently hydrogen, halogen, $NR_{19}R_{20}$, $OR_{19}$, $SR_{19}$, alkyl of from one to three carbon atoms, wherein $R_{19}$ and $R_{20}$ are each independently hydrogen, alkyl of from one to three carbon atoms, or acyl of from one to three carbon atoms;

W is O, $NR_{21}$, S or $CH_2$ wherein $R_{21}$ is hydrogen, alkyl of from one to three carbon atoms, hydroxyalkyl of from two to three carbon atoms, benzyl or p-aminobenzyl;

X is CH, CF, N, CCl, CBr, or C—$CF_3$;

Y is hydrogen, fluoro, or amino;

$R_1$ is hydrogen, alkyl having from one to six carbon atoms or a cation;

$R_2$ is an alkyl of from one to four carbon atoms, vinyl, haloalkyl, hydroxyalkyl of from two to four carbon atoms, or a cycloalkyl of from three to six carbon atoms, phenyl, or substituted phenyl wherein the substituents on the phenyl are halogen, amino, hydroxy, alkyl, or alkoxy;

$R_3$ is hydrogen or an alkyl of from one to three carbon atoms;

$R_4$ is hydrogen or an alkyl of from one to three carbon atoms;

or a pharmaceutically acceptable acid addition or base salt thereof.

Preferred compounds of the invention are those wherein Y is hydrogen or amino, $R_1$ is hydrogen or a pharmaceutically acceptable salt thereof, $R_2$ is cyclopropyl, ethyl, 2-fluoroethyl, hydroxyethyl, vinyl or substituted phenyl, and Z is selected from -continued

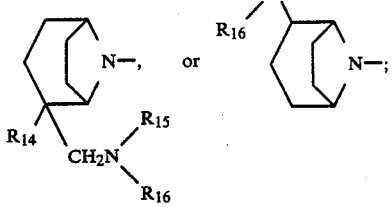

wherein $R_{11}$ is hydrogen and $R_{12}$ is methyl or ethyl; $R_{14}$ is hydrogen and $R_{13}$ is $CH_2NR_{15}R_{16}$ wherein $R_{15}$ and $R_{16}$ are each independently hydrogen, methyl, or ethyl.

Other preferred compounds of the invention are those wherein Y is hydrogen.

Still other preferred compounds of the present invention are those wherein $R_2$ is ethyl, vinyl, 2-fluoroethyl, or cyclopropyl.

Yet other preferred compounds of the invention are those wherein $R_1$ is hydrogen or a cation.

Particularly preferred compounds of the invention are:

7-(2-azabicyclo[2.2.1]heptane)-6,8-difluoro-1-cyclopropyl-1,4-dihydro-4-oxo-3-quinolinecarboxylic acid, 7-(6,8-diazabicyclo[3.2.2]non-6-yl]-1-ethyl-6,8-difluoro-1,4-dihydro-4-oxo-3-quinolinecarboxylic acid, 1-cyclopropyl-7-(6,8-diazabicyclo[3.2.2]non-6-yl)-6,8-difluoro-1,4-dihydro-4-oxo-3-quinolinecarboxylic acid, 1-cyclopropyl-7-(6,8-diazabicyclo[3.2.2]non-6-yl)-6-fluoro-1,4-dihydro-4-oxo-1,8-naphthyridine-3carboxylic acid, 1-ethyl-6,8-difluoro-1,4-dihydro-7-(8-methyl-6,8-diazabicyclo[3.2.2]non-6-yl)-4-oxo-3-quinolinecarboxylic acid, 1-cyclopropyl-7-[3-endo(dimethylamino)-8-azabicyclo[3.2.1]oct-8-yl]-6-fluoro-1,4-dihydro-4-oxo-1,8-naphthyridine-3-carboxylic acid, 1-cyclopropyl-7-[3-endo(dimethylamino)-8-azabicyclo[3.2.1]oct-8-yl]-6-fluoro-1,4-dihydro-4-oxo-3-quinolinecarboxylic acid, 1-cyclopropyl-7-[3-endo(dimethylamino)-8-azabicyclo[3.2.1]oct-8-yl]-6,8-difluoro-1,4-dihydro-4-oxo-3-quinolinecarboxylic acid, 1-cyclopropyl-6-fluoro-1,4-dihydro-7-[2-endo(methylamino)-8-azabicyclo[3.2.1]oct-8-yl]-4-oxo-1,8-naphthyridine-3-carboxylic acid, 1-cyclopropyl-6-fluoro-1,4-dihydro-7-[3-endo(ethylamino)-8-azabicyclo[3.2.1]oct-8-yl]-4-oxo-1,8-naphthyridine-3-carboxylic acid, 1-cyclopropyl-6-fluoro-1,4-dihydro-7-[2-endo(methylamino)-8-azabicyclo[3.2.1]oct-8-yl]-4-oxo-3-quinolinecarboxylic acid, 1-cyclopropyl-6,8-difluoro-1,4-dihydro-7-2-endo(methylamino)-8-azabicyclo[3.2.1]oct-8-yl]-4-oxo-3-quinolinecarboxylic acid, 1-cyclopropyl-6-fluoro-1,4-dihydro-7-(1-methyl-6,8-diazabicyclo[3.2.2]non-yl)-4-oxo-1,8-naphthyridine-3-carboxylic acid, 1-cyclopropyl-6-fluoro-1,4-dihydro-7-(1-methyl-6,8-diazabicyclo[3.2.2]non-6-yl)-4-oxo-3-quinolinecarboxylic acid, 1-cyclopropyl-6,8-difluoro-1,4-dihydro-7-(1-methyl-6,8-diazabicyclo[3.2.2]non-6-yl)-4-oxo-3-quinolinecarboxylic acid, 1-cyclopropyl-6-fluoro-1,4-dihydro-7-(6-methyl-2,5-iazabicyclo[2.2.1]hept-2-yl)-4-oxo-1,8-naphthyridine-3-carboxylic acid, 1-cyclopropyl-6-fluoro-1,4-dihydro-7-(6-methyl-2,5-diazabicyclo[2.2.1]hept-2-yl)-4-oxo-3-quinolinecarboxylic acid, 1-cyclopropyl-7-(6,8-diazabicyclo[3.2.2]non-6-yl)-6-fluoro-1,4-dihydro-4-oxo-3-quinolinecarboxylic acid, 1-cyclopropyl-6,8-difluoro-1,4-dihydro-7-(6-methyl-2,5-diazabicyclo[2.2.1]hept-2-yl)-4-oxo-3-quinolinecarboxylic acid, 1-cyclopropyl-8-chloro-7-(6,8-diazabicyclo[3.2.2]-non-6-yl)-6-fluoro-1,4-dihydro-4-oxo-3-quinolinecarboxylic acid, 1-cyclopropyl-5-amino-7-(6,8-diazabicyclo[3.2.2]-non-6-yl)-6,8-difluoro-1,4-dihydro-4-oxo-3-quinolinecarboxylic acid, 1-cyclopropyl-5-amino-6,8-difluoro-1,4-dihydro-7-(1-methyl-6,8-diazabicyclo[3.2.2]non-6-yl)-4-oxo-3-quinolinecarboxylic acid, 1-cyclopropyl-7-[3-exo(ethylamino)-8-azabicyclo[3.2.1]oct-8-yl]-6-fluoro-1,4-dihydro-4-oxo-1,8-naphthyridine-3-carboxylic acid, 1-cyclopropyl-7-[3-endo(ethylamino)-8-azabicyclo[3.2.1]oct-8-yl]-6,8-difluoro-1,4-dihydro-4-oxo-3-quinolinecarboxylic acid, 1-cyclopropyl-7-[3-exo(ethylamino)-8-azabicyclo[3.2.1]oct-8-yl]-6,8-difluoro-1,4-dihydro-4-oxo-3-quinolinecarboxylic acid, 1-cyclopropyl-7-[3-endo(ethylamino)-8-azabicyclo[3.2.1]oct-8-yl]-6-fluoro-1,4-dihydro-4-oxo-3-quinolinecarboxylic acid, 1-cyclopropyl-7-[3-exo(ethylamino)-8-azabicyclo[3.2.1]oct-8-yl]-6-fluoro-1,4-dihydro-4-oxo-3-quinolinecarboxylic acid, 1-cyclopropyl-8-chloro-7-(1-methyl-6,8-diazabicyclo[3.2.2]non-6-yl)-6-fluoro-1,4-dihydro-4-oxoquinoline-3-carboxylic acid, 1-ethyl-7-(1-methyl-6,8-diazabicyclo[3.2.2]non-6-yl)-6,8-difluoro-1,4-dihydro-4-oxo-quinoline-3-carboxylic acid, 1-cyclopropyl-6,8-difluoro-7-(8-methyl-6,8-diazabicyclo[3.2.2]non-6-yl)-1,4-dihydro-4-oxoquinoline-3-carboxylic acid, 1-cyclopropyl-6-fluoro-7-(8-methyl-6,8-diazabicyclo[3.2.2]non-6-yl)-1,4-dihydro-4-oxo-quinoline-3-carboxylic acid, 1-cyclopropyl-6-fluoro-7-(8-methyl-6,8-diazabicyclo[3.2.2]non-6-yl)-1,4-dihydro-4-oxo-1,8-naphthyridine-3-carboxylic acid, 1-cyclopropyl-6-fluoro-8-chloro-7-(8-methyl-6,8-diazabicyclo[3.2.2]non-6-yl)-1,4-dihydro-4-oxoquinoline-3-carboxylic acid, 1-cyclopropyl-5-amino-6,8-difluoro-7-(8-methyl-6,8-diazabicyclo[3.2.2]non-6-yl)-1,4-dihydro-4-oxoquinoline-3-carboxylic acid, 1-cyclopropyl-6-fluoro-8-chloro-7-(6-methyl-2,5-diazabicyclo[2.2.1]hept-2-yl)-1,4-dihydro-4-oxoquinoline-3-carboxylic acid, 1-cyclopropyl-6,8-difluoro-5-amino-7-(6-methyl-2,5-diazabicyclo[2.2.1]hept-2-yl)-1,4-dihydro-4-oxoquinoline-3-carboxylic acid, 1-cyclopropyl-6-fluoro-7-(5,6-dimethyl-2,5-diazabicyclo[2.2.1]hept-2-yl)-1,4-dihydro-4-oxoquinoline-3-carboxylic acid,
1-cyclopropyl-6,8-difluoro-7-(5,6-dimethyl-2,5-diazabicyclo[2.2.1]hept-2-yl)-1,4-dihydro-4-oxoquinoline-3-carboxylic acid,
1-cyclopropyl-6-fluoro-7-(5,6-dimethyl-2,5-diazabicyclo[2.2.1]hept-2-yl)-1,4-dihydro-4-oxo-1,8-naphthyridine-3-carboxylic acid,
1-cyclopropyl-6,8-difluoro-5-amino-7-(5,6-dimethyl-2,5-diazabicyclo[2.2.1]hept-2-yl)-1,4-dihydro-4-oxoquinoline-3-carboxylic acid,
1-cyclopropyl-6-fluoro-8-chloro-7-(5,6-dimethyl-2,5-diazabicyclo[2.2.1]hept-2-yl)-1,4-dihydro-4-oxoquinoline-3-carboxylic acid,
1-cyclopropyl-7-(1,8-dimethyl-6,8-diazabicyclo[3.2.2]non-6-yl)-6,8-difluoro-1,4-dihydro-4-oxoquinoline-3-carboxylic acid,
1-cyclopropyl-7-(1,8-dimethyl-6,8-diazabicyclo[3.2.2]non-6-yl)-6-fluoro-1,4-dihydro-4-oxoquinoline-3-carboxylic acid,
1-cyclopropyl-7-(1,8-dimethyl-6,8-diazabicyclo[3.2.2]non-6-yl)-6-fluoro-8-chloro-1,4-dihydro-4-oxoquinoline-3-carboxylic acid,
1-cyclopropyl-7-(1,8-dimethyl-6,8-diazabicyclo[3.2.2]non-6-yl)-5-amino-6,8-difluoro-1,4-dihydro-4-oxoquinoline-3-carboxylic acid,
1-cyclopropyl-7-(1,8-dimethyl-6,8-diazabicyclo[3.2.2]non-6-yl)-6-fluoro-1,4-dihydro-4-oxo-1,8-naphthyridine-3-carboxylic acid,
1-cyclopropyl-6-fluoro-8-chloro-[3-endo(ethylamino)-8-azabicyclo[3.2.1]oct-8-yl]-1,4-dihydro-4-oxoquinoline-3-carboxylic acid,
1-cyclopropyl-6,8-difluoro-5-amino-[3-endo(ethylamino)-8-azabicyclo[3.2.1]oct-8-yl]-1,4-dihydro-4-oxo-quinoline-3-carboxylic acid,
1-cyclopropyl-6-fluoro-8-chloro-[3-exo(ethylamino)-8-azabicyclo[3.2.1]oct-8-yl]-1,4-dihydro-4-oxoquinoline-3-carboxylic acid,
1-cyclopropyl-6,8-difluoro-5-amino-[3-exo(ethylamino)-8-azabicyclo[3.2.1]oct-8-yl]-1,4-dihydro-4-oxo-quinoline-3-carboxylic acid,
1-cyclopropyl-6-fluoro-8-chloro-[3-endo(methylamino)-8-azabicyclo[3.2.1]oct-8-yl]-1,4-dihydro-4-oxo-quinoline-3-carboxylic acid,
1-cyclopropyl-6,8-difluoro-5-amino-[3-endo(methylamino)-8-azabicyclo[3.2.1]oct-8-yl]-1,4-dihydro-4-oxo-quinoline-3-carboxylic acid,
1-cyclopropyl-6-fluoro-8-chloro-[3-exo(methylamino)-8-azabicyclo[3.2.1]oct-8-yl]-1,4-dihydro-4-oxo-quinoline-3-carboxylic acid, and
1-cyclopropyl-6,8-difluoro-5-amino-[3-exo(methylamino)-8-azabicyclo[3.2.1]oct-8-yl]-1,4-dihydro-4-oxo-quinoline-3-carboxylic acid.

The invention includes a process for preparing compounds of the formula:

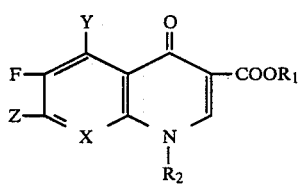

or

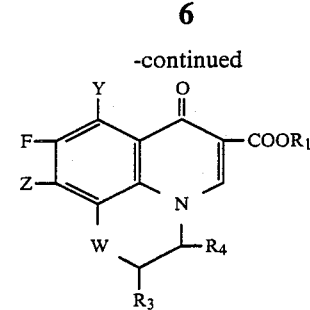

wherein $R_1$, $R_2$, $R_3$, $R_2$, W, X, Y, and Z are as defined above which comprises reacting a compound having the following structural formula:

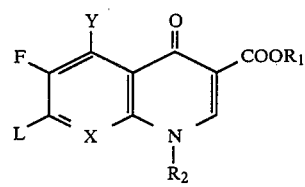

or

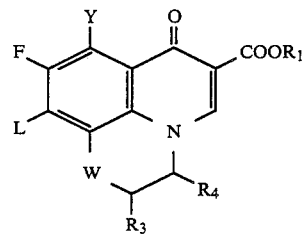

with an amine corresponding to the group Z-H wherein Z is a compound of the formula:

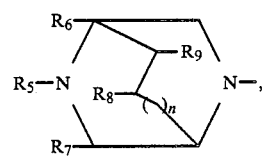

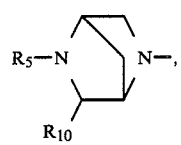

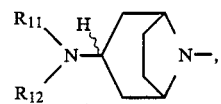

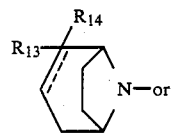

-continued

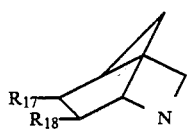
(e)

wherein all of the above terms are as defined in formula I and II and L is a leaving group which is halogen or an alkylsulfonyl group of from one to three carbon catoms, preferably fluorine, chlorine, methane- or ethanesulfonyl.

Another aspect of the invention is a novel process for the preparation of compounds of the formula

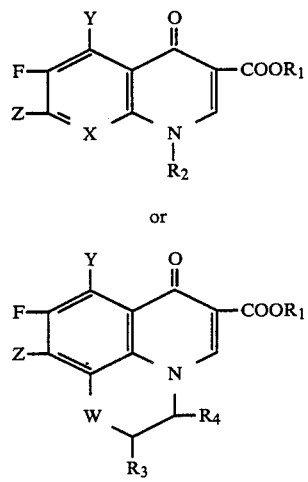

wherein Z is

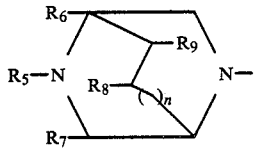
VI and wherein $R_5$, $R_6$, $R_7$, $R_8$, $R_9$, or n are as described above.

Another aspect of the present invention are compounds:
6-methyl-2,5-diazabicyclo[2.2.1]heptane,
1-methyl-6,8-diazabicyclo[3.2.2]nonane.

Yet another aspect of the present invention is a process for the preparation of a 6,8-diazabicyclo [3.2.2]nonane, dihydrochloride of the formula

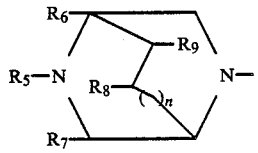
(a)

as described hereinafter.

Another aspect of the invention is a pharmaceutical composition which comprises an antibacterially effective amount of a compound of formula I or II or any of the particularly preferred compound as recited above and the pharmaceutically acceptable salts thereof in combination with a pharmaceutically acceptable carrier.

Another aspect of the invention is a method for treating bacterial infections in a mammal which comprises administering an antibacterially effective amount of the above defined pharmaceutical composition in unit dosage form to a mammal in need thereof.

DETAILED DESCRIPTION OF THE INVENTION

The compounds of the invention having the structural formula I and II may be prepared by treating a corresponding compound having the structural formula III or IV with the desired cyclic amine Z. For purposes of this reaction, the amine substituent of compound Z may, if desired, be protected or masked by a group which renders it substantially inert to the reaction conditions or removes the basicity of the nitrogen. Such groups are, for example: carboxylic acid acyl groups such as formyl, acetyl, trifluoroacetyl; alkoxycarbonyl groups such as ethoxycarbonyl, t-butoxycarbonyl, $\beta,\beta,\beta$-trichloroethoxycarbonyl, $\beta$-iodoethoxycarbonyl; aryloxycarbonyl groups such as benzyloxycarbonyl, p-methoxybenzyloxycarbonyl, phenoxycarbonyl; amino acids and substituted amino acids such as glycyl, alanyl, aspartyl, glutamyl, lysyl, phenylalanyl; silyl groups such as trimethylsilyl; and groups such as trityl, tetrahydropyranyl, vinyloxycarbonyl, o-nitrophenylsulfenyl, diphenylphosphinyl, p-toluenesulfonyl, and benzyl, may all be utilized. The protecting group may be removed, after the reaction between compound III or IV and compound Z, if desired, by procedures known to those skilled in the art. For example, the ethoxycarbonyl group may be removed by acid or base hydrolysis and the trityl group may be removed by hydrogenolysis or acid hydrolysis.

The reaction between the compound of structural formula III or IV and a suitably protected compound of formula Z may be performed with or without a solvent, preferably at elevated temperature for a sufficient time so that the reaction is substantially complete. The reaction is preferably carried out in the presence of an acid acceptor such as an alkali metal or alkaline earth metal carbonate or bicarbonate, a tertiary amine such as triethylamine, 1,8-diazabicyclo[5.4.0]undec-7-ene (DBU), pyridine, or picoline. Alternatively an excess of a compound formula Z may be utilized as the acid acceptor.

Convenient solvents for this reaction are non-reactive solvents such as acetonitrile, tetrahydrofuran, ethanol, chloroform, dimethylsulfoxide, dimethylformamide, pyridine, picoline, water, and the like. Solvent mixtures may also be utilized.

Convenient reaction temperatures are in the range of from about 20° to about 150° C.; higher temperatures usually require shorter reaction times.

The removal of the protecting group may be accomplished either before or after isolating the product, I or II. Alternatively, the protecting group need not be removed.

The starting compounds having structural formulae III and IV are known in the art or, if new, may be prepared from known starting materials by standard procedures or by variations thereof. Thus, the following compounds are disclosed in the noted references:

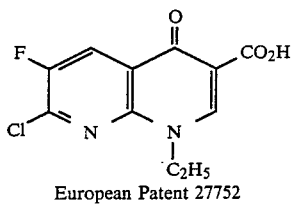
European Patent 27752

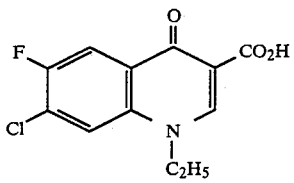
J. Med. Chem., 23, 1358 (1980)

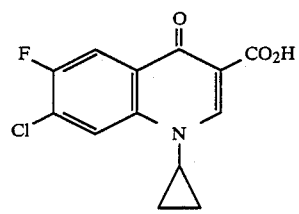
European Patent Publication 0078362

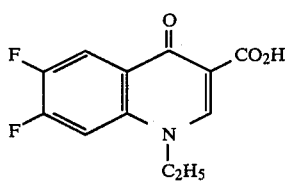
European Patent 0,000,203

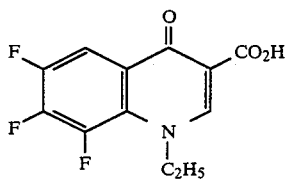
British Patent 2,057,440

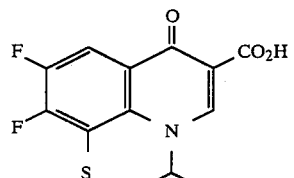
Japanese Patent Publication 7203-085

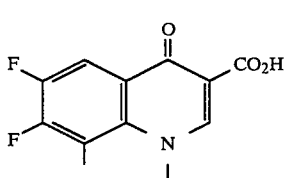
European Patent 47005

-continued

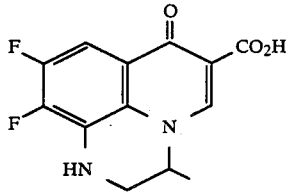
Japanese Patent Publication 7203-085

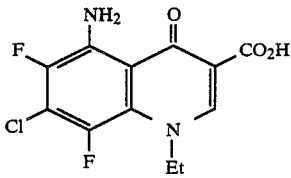
Japanese Patent Publication 8174 367-A

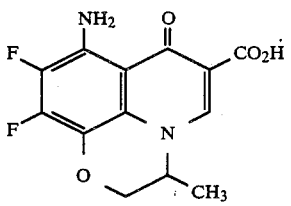
Japanese Patent Publication 7149-286

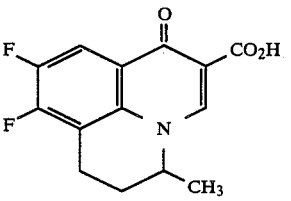
British Patent 2057 440

1-Cyclopropyl-6,7,8-trifluoro-1,4-dihydro-4-oxo-3-quinolinecarboxylic acid may be prepared by a series of reactions starting from 2,3,4,5-tetrafluorobenzoic acid. The sodium salt of 2,3,4,5-tetrafluorobenzoic acid is reacted with oxalyl chloride and the product condensed with diethyl malonate in the presence of magnesium turnings to afford after hydrolysis 2,3,4,5-tetrafluorobenzoylacetic acid, ethyl ester.

This compound is, in turn, treated with triethylorthoformate and acetic anhydride, followed by cyclopropylamine to afford 2-(2,3,4,5-tetrafluorobenzoyl)-2-cyclopropylaminoacrylic acid, ethyl ester, which is then ring closed with sodium hydride and hydrolysed to give the desired intermediate.

7-Chloro-1-cyclopropyl-6 0fluoro-1,4-dihydro-4-oxo-1,8-naphthyridine-3-carboxylic acid may be prepared by a series of reactions starting from 4-(6-chloro-3-nitro-2-pyridinyl)-1-piperazinecarboxylic acid, ethyl ester. The intermediate, 1-cyclopropyl-6-fluoro-1,4-dihydro-4-oxo-7-(1-piperazinyl)-1,8-naphthyridine-3-carboxylic acid can be converted to the 7-hydroxy derivative with a mixture of nitric and sulfuric acids which is then replaced by chlorine by treatment with phosphorus oxychloride to give the desired intermediate.

Some of the compounds of the invention having formula Z are either known compounds or they may be prepared from known starting materials by standard procedures or by variations thereof. For example, exo and endo-3-amino-8-azabicyclo[3.2.1]octanes having the structural formula A and the acetyl derivatives B,

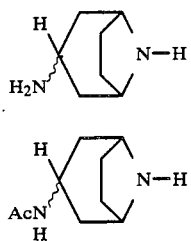

may be readily prepared from the known starting material 8-(phenylmethyl-8-azabicyclo[3.2.1]octan-3-one oxime, [J. R. Bagley and T. N. Riley, J. Heterocyclic Chem., 19, 485 (1982)] by the following reaction sequence.

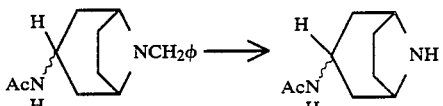

Certain compounds of the invention having formula Z wherein Z is

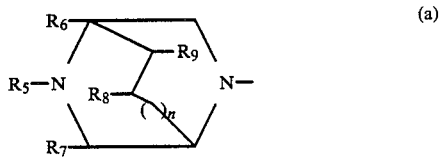

are made by a novel process described hereinafter according to Scheme I below.

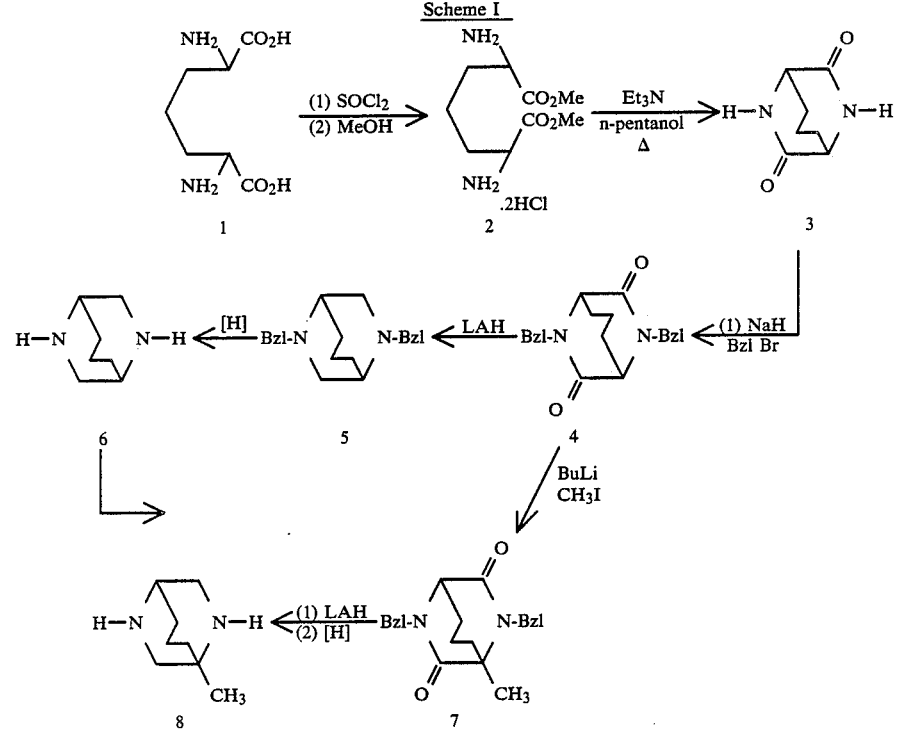

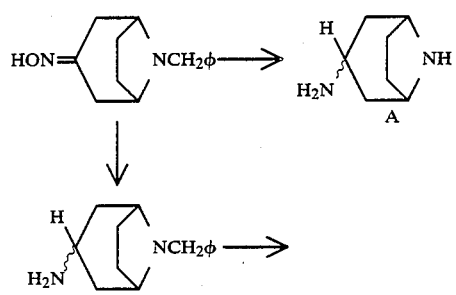

The novel bridged compounds of the present invention are prepared by esterifying a 2,6-diaminoheptanedioic acid (1), preferably with thionyl chloride and methanol, to form the corresponding 2,6-diaminoheptanedioic acid dimethyl ester, hydrochloride (2). The 2,6-diaminoheptanedioic acid may be substituted at the 2,3, or 4-positions each independently by an alkyl, preferably by a methyl group. The reaction proceeds at reflux and then is stirred for from 10 to 20 hours or overnight at room temperature.

The esterified compound is then reacted with a trialkylamine and an alcohol such as, for example, 1-pentanol to form the corresponding 6,8-diazabicyclo[3.2.2]nonane-7,9-dione (3). The triethylamine is the preferred reactant. A dilute solution is used. It is heated under reflux for as long as four days.

The dione formed is reacted with an alkali metal hydride, preferably sodium hydride, and an unsubstituted or substituted benzylhalide to form the corresponding 6,8-bis(substituted or unsubstituted benzyl)-6,8-diazabicyclo[3.2.2]nonane-7,9-dione (4). The benzyl group may be substituted by an alkyl of from one to four, an alkoxy, or a halogen group. The benzyl group methylene may be substituted by alkyl, preferably by a methyl group. Preferably bromomethylbenzene or an α-methyl benzyl halide such as chlorine, bromine, or iodine is used.

Alternatively when it is desired to prepare the dione substituted by, for example, a methyl group, the dione is reacted with butyllithium and an alkyl halide to form the corresponding bridgehead alkyl-substituted 6,8-bis(substituted phenyl)-6,8-diazabicyclo[3.2.2]nonane-7,9-dione (7).

The above bis-benzylated dione-containing compound is then reduced to the corresponding 6,8-bis(substituted or unsubstituted benzyl)-6,8-diazabicyclo[3.2.2]nonane (7 or 5) with lithium aluminum hydride in tetrahydrofuran, diglyme, ether, diethylether or dioxane. Preferably tetrahydrofuran is used. The reduced compound is subsequently debenzylated by catalytic hydrogenation, preferably palladium on carbon, to form a desired 6,8-diazabicyclo[3.2.2]nonane, hydrochloride (6 or 8). The reaction occurs in methanol and water in a ratio of about 2:1.

The desired 6,8-diazabicyclo[3.2.2]nonane hydrochloride or dihydrochloride or free base and 1,8-diazabicyclo[5.4.0]undec-7-ene is reacted with a compound of formula I or II as described hereinabove to form the desired compound and converting, if desired, to a pharmaceutically acceptable salt thereof.

Other novel bridged compounds of the present invention, such as, for example, in the formula for Z (b)

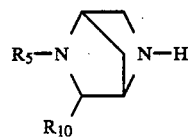

may be prepared from 4-hydroxy-5-methylproline (H. Brockmann and E. A. Staehler, Naturwissonschaften, 52, 391 (1965). CA 63:8477b (1965).) by a method analogous to that of P. S. Portoghese and A. A. Mikhail, J. Org. Chem., 31, 1059 (1966). Scheme II below is illustrative of this analogous method.

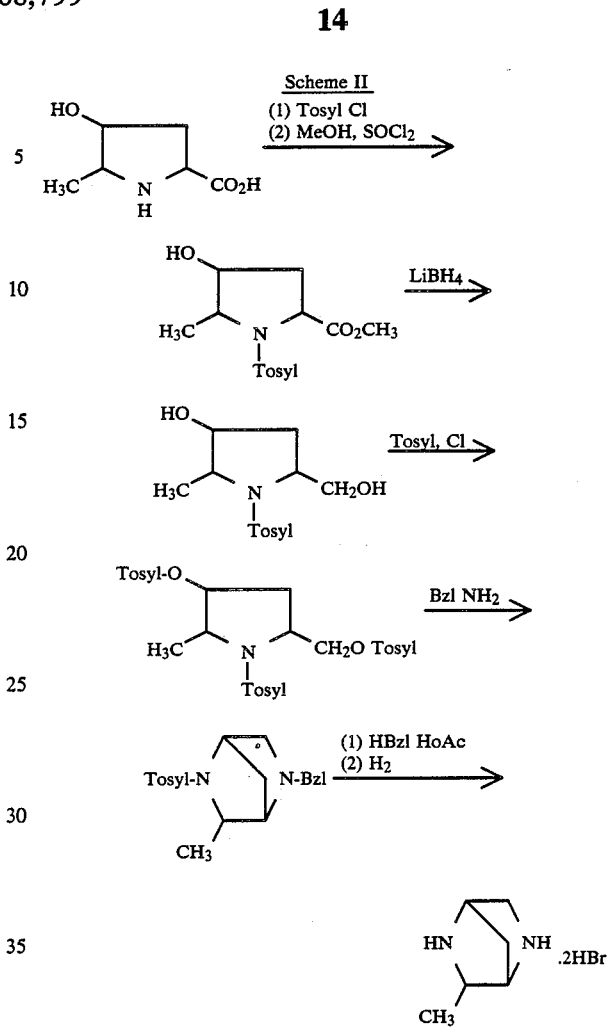

The compounds of the invention display antibacterial activity when tested by the microtitration dilution method as described in Heifetz, et al, Antimicr. Agents & Chemoth., 6, 124 (1974), which is incorporated herein by reference.

By use of the above reference method, the following minimum inhibitory concentration value (MICs in μg/ml) shown in Table I were obtained for representative compounds of the invention.

TABLE I

| IN VITRO ANTIBACTERIAL ACTIVITY MINIMAL INHIBITORY CONCENTRATION MIC (μg/ml) | | | | | | |
|---|---|---|---|---|---|---|
| Organism | Ex. 5d | Ex. 5a | Ex. 5c | Ex. 5b | Ex. 5f | Ex. 5e |
| *Enterobacter cloacae* MA 2646 | 0.2 | 0.8 | 0.4 | 0.8 | 1.6 | 0.8 |
| *Escherichia coli* Vogel | 0.2 | 0.2 | 0.4 | 0.4 | 1.6 | 0.4 |
| *Klebsiella pneumoniae* MGH-2 | 0.4 | 0.4 | 0.8 | 0.8 | 3.1 | 0.8 |
| *Proteus rettgeri* M 1771 | 1.6 | 3.1 | 3.1 | 3.1 | 12.5 | 3.1 |
| *Pseudomonas aeruginosa* UI-18 | 3.1 | 1.6 | 3.1 | 3.1 | 6.3 | 3.1 |
| *Staphylococcus aureus* H 228 | 0.2 | 0.2 | 0.8 | 0.8 | 3.1 | 0.4 |
| *Staphylococcus aureus* UC-76 | 0.1 | 0.2 | 0.2 | 0.4 | 0.8 | 0.2 |
| *Streptococcus faecalis* MGH-2 | 0.2 | 0.4 | 0.8 | 0.8 | 3.1 | 0.4 |
| *Streptococcus pneumoniae* SV-1 | 0.1 | 0.2 | 0.4 | 0.4 | 1.6 | 0.2 |
| *Streptococcus pyogenes* C-203 | 0.1 | 0.4 | 0.4 | 0.4 | 1.6 | 0.4 |
| Organism | Ex. 1 | Ex. 4 | Ex. 2 | Ex. 3 | Ex. 7 | Ex. 8 |
| *Enterobacter cloacae* MA 2646 | 0.4 | 1.6 | 0.1 | 0.05 | 0.05 | 0.2 |
| *Escherichia coli* Vogel | 0.4 | 0.8 | 0.4 | 0.03 | 0.05 | 0.2 |
| *Klebsiella pneumoniae* MGH-2 | 0.8 | 1.6 | 0.2 | 0.1 | 0.1 | 0.2 |
| *Proteus rettgeri* M 1771 | 0.8 | 6.3 | 0.4 | 0.4 | 0.4 | 0.4 |
| *Pseudomonas aeruginosa* UI-18 | 3.1 | 12.5 | 0.8 | 0.4 | 0.4 | 0.8 |

TABLE I-continued

IN VITRO ANTIBACTERIAL ACTIVITY
MINIMAL INHIBITORY CONCENTRATION
MIC (µg/ml)

| | | | | | | |
|---|---|---|---|---|---|---|
| Staphylococcus aureus H 228 | 0.2 | 0.2 | 0.05 | 0.2 | 0.1 | 0.2 |
| Staphylococcus aureus UC-76 | 0.05 | 0.1 | 0.05 | 0.1 | 0.025 | 0.05 |
| Streptococcus faecalis MGH-2 | 0.8 | 0.8 | 0.2 | 0.2 | 0.1 | 0.2 |
| Streptococcus pneumoniae SV-1 | 0.8 | 0.8 | 0.2 | 0.05 | 0.05 | 0.1 |
| Streptococcus pyogenes C-203 | 1.6 | 1.6 | 0.8 | 0.1 | 0.05 | 0.1 |

The compounds of the invention are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

Pharmaceutically acceptable acid additional salts are formed with organic and inorganic acids.

Examples of suitable acids for salt formation are hydrochloric, sulfuric, phosphoric, acetic, citric, oxalic, lactic, malonic, salicyclic, malic, gluconic, fumaric, succinic, ascorbic, maleic, methanesulfonic, and the like. The salts are prepared by contacting the free base form with a sufficient amount of the desired acid to produce either a mono or di, etc. salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where $R_1$ is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about four carbon atoms except when specifically stated to be greater than four carbon atoms. Representative of such groups are methyl, ethyl, propyl, isopropyl, butyl, tertiary butyl and the like.

The alkoxy groups contemplated by the invention comprise both straight and branched carbon chains of from one to about six carbon atoms unless otherwise stated. Representative of such groups are methoxy, ethoxy, propoxy, i-propoxy, t-butoxy, hexoxy, and the like.

The cycloalkyl groups contemplated by the invention comprise those having three to six carbon atoms such as cyclopropyl, cyclobutyl, cyclopentyl, and cyclohexyl. The cycloalkyl groups may be substituted by halogen, amine, hydroxy, or alkyl.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2-propyl, γ-iodobutyl, and the like.

The acyl group is intended to include carbon chains of from one to three carbon atoms except when specifically stated to be greater than three carbon atoms. Included in the scope of the invention are, for example, formyl, acetyl and propionyl.

The term halogen is intended to include fluorine, chlorine, bromine, and iodine unless otherwise specified.

Phenyl includes substituted phenyl wherein the substituents may be halogen, amine, alkoxy, hydroxy, or alkyl.

Certain compounds of the invention may exist in optically active forms. The pure dextrorotatory isomer, pure levorotatory isomer as well as mixtures thereof; including the racemic mixtures, optical isomers, and all permutations of the possible enantiomorphs where more than one chiral center exists within the molecule, are contemplated by the invention. Pure endo and pure exo and mixtures thereof are also contemplated. Additional assymmetric carbon atoms may be present in a substituent such as an alkyl group. All such isomers as well as mixtures thereof are intended to be included in the invention.

The compounds of the invention can be prepared and administered in a wide variety of oral and parenteral dosage forms. It will be obvious to those skilled in the art that the following dosage forms may comprise as the active component, either a compound of formula I or II or a corresponding pharmaceutically acceptable salt of a compound of formula I or II.

For preparing pharmaceutical compositions from the compounds described by this invention, inert, pharmaceutically acceptable carriers can be either solid or liquid. Solid form preparations include powders, tablets, dispersable granules, capsules, cachets, and suppositories. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example may be mentioned water or water-propylene glycol solutions for parenteral injection. Such solutions are prepared so as to be acceptable to biological systems (isotonicity, pH, etc.). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections, the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate methods for preparing the compounds of the invention.

PREPARATION OF STARTING MATERIALS

Example A 2,6-Diaminoheptanedioic acid, dimethyl ester, dihydrochloride

To a suspension of 75.0 g (0.394M) of 2,6-diaminoheptanedioic acid and 2.5 L of methanol, 64 ml (0.87M) of thionyl chloride was slowly added. The resulting warm solution was heated under reflux for 5 hr and stirred overnight at room temperature. The solution was evaporated to dryness and the residue was recrystallized from methanol-ether to give 111.2 g of the title compound, mp 183°-186° dec (97%).

6,8-Diazabicyclo[3.2.2]nonane-7,9-dione

A solution of 39.0 g (0.134M) of 2,6-diaminoheptanedioic acid, dimethyl ester, dihydrochloride, 56 ml (0.4M) of triethylamine, and 3 L of 1-pentanol was heated under reflux for 4 days. The solution was evaporated to dryness and the residue was recrystallized from chloroform to give 14.3 g of the title compound, mp 280°-283° (69%).

6,8-Bis(phenylmethyl)-6,8-diazabicyclo[3.2.2]nonane-7,9-dione

A solution of 14.26 g (92.5 mmol) of 6,8-diazabicyclo[3.2.2]nonane-7,9-dione, 450 ml of DMF, and 11.1 g (231 mmol) of 50% by wt. sodium hydride dispersion in oil was stirred at room temperature and then added 24.8 ml (208 mmol) of (bromomethyl)benzene dropwise over 5 min. The resulting hot solution was stirred without external heating for 1.75 hr and then poured into 1 L of water with stirring. The solid was collected by filtration, washed with water and ether and recrystallized from 2-propanol to give 26.9 g of the title compound, mp 201°-2° (87%).

6,8-Diazabicyclo[3.2.2]nonane, dihydrochloride

To a slurry of 15.18 g (0.40M) of lithium aluminum hydride in 250 ml of THF was added a slurry of 22.3 g (66.7 mmol) of 6,8-bis(phenylmethyl)-6,8-diazabicyclo[3.2.2]nonane-7,9-dione (Aust. J. Chem., 1982, 35, 2289-98) in 1 L of THF over a 10 minute period. The reaction mixture was stirred at room temperature for 1 hr and heated under reflux for 19 hrs. To the cooled reaction mixture 23.2 ml of water was added dropwise. The inorganic salts were removed by filtration and the THF solution was evaporated to give 18.6 g of an oil. This oil was dissolved with 500 ml of ether and 23 ml of 6N HCl in 2-propanol was added. The 6,8-bis(phenylmethyl)-6,8-diazabicyclo[3.2.2]nonane, dihydrochloride was isolated by filtration and washed with ether to give 20.3 g, mp 160°-165° dec (80%).

A solution of 20.28 g (53.5 mmol) of 6,8-bis(phenylmethyl)-6,8-diazabicyclo[3.2.2]nonane dihydrochloride in 400 of 2:1 methanol-water was hydrogenated using 2.5 g of 20% Pd/C catalyst. The reaction mixture was filtered and evaporated to dryness. The residue was triturated with 2-propanol and filtered to give 9.84 g of 6,8-diazabicyclo[3.2.2]nonane, dihydrochloride, mp 300°-310° dec (92%).

Example B 3-(Exo-ethylamino)-8-(phenylmethyl)-8-azabicyclo[3.2.1]octane, dihydrochloride A solution of 8.2 g (25.8 mmol) of 3-(exo-acetylamino)-8-(phenylmethyl)-8azabicyclo[3.2.1]octane (M. P. Hutt et al., U.S. Pat. No. 4,571,396) in 100 ml THF was slowly added to a suspension of 5.88 g (155 mmol) LiALH$_4$ in 100 ml of THF. The resulting mixture was heated under reflux for 18 hrs. After cooling to room temperature, 9.0 ml of water was added dropwise. After the mixture cooled to room temperature, it was filtered and the inorganic salts were washed with THF. The filtrate was evaporated to 5.9 g of oil which was dissolved with 200 ml of ether and 6N HCl in isopropyl alcohol added to form the HCl salt, 7.08 g, mp 250°-255° C. dec.

3-(Exo-ethylamino)-8-azabicyclo[3.2.1]octane, dihydrochloride

A solution of 6.88 g (21.7 mmol) of 3-(exo-ethylamino)-8-(phenylmethyl)-8-azabicyclo[3.2.1]octane, dihydrochloride, 80 ml of methanol and 20 ml of water was hydrogenated over 1 g of 20% Pd/C until the requisite hydrogen uptake was recorded. The reaction mixture was filtered and the filtrate was evaporated to dryness and the residue was triturated with isopropanol to give 4.22 g of the title compound, mp 250°-270° dec.

Example C 3-(Endo-ethylamino)-8-azabicyclo[3.2.1]octane, dihydrochloride

In a similar manner as described in Example B, 3.8 g of 3-(endo-acetylamino)-8-(phenylmethyl)-8-azabicyclo[3.2.1]octane (M. P. Hutt et al, U.S. Pat. No. 4,571,396) was reduced with LiAlH converted to the hydrochloride salt, and debenzylated to give the title compound as a hygroscopic glassy solid.

PREPARATION OF FINAL PRODUCTS

Example 1

7-(6,8-Diazabicyclo[3.2.2]non-6-yl)-1-ethyl-6,8-difluoro-1,4-dihydro-4-oxo-3-quinolinecarboxylic acid A solution of 0.81 g (3.0 mmol) of 1-ethyl-6,7,8-trifluoro-1,4-dihydro-4-oxo-3-quinolinecarboxylic acid, 0.66 g (3.3 mmol) of 6,8-diazabicyclo[3.2.2]nonane, dihydrochloride, 1.35 ml (9.0 mmol) of 1,8-diazabicyclo[5.4.0]undec-7-ene and 20 ml of acetonitrile was heated under reflux for 3 hr. After cooling to room temperature the solid was collected by filtration to give 0.52 g of the title compound, mp 245°-250°.

Example 2

1-Cyclopropyl-7-(6,8-diazabicyclo[3.2.2]non-6-yl)-6,8-difluoro-1,4-dihydro-4-oxo-3-quinolinecarboxylic 7 acid A mixture of 0.71 g (2.5 mmol) of 1-cyclopropyl-6,7,8-trifluoro-1,4-dihydro-4-oxo-3-quinolinecarboxylic acid, 0.54 g (2.7 mmol) of 6,8-diazabicyclo[3.2.2]nonane, dihydrochloride, 1.13 ml (7.5 mmol) of 1,8-diazabicyclo[5.4.0]undec-7-ene and 15 ml of acetonitrile was heated under reflux for 1.5 hr. The reaction mixture was stirred overnight at room temperature and filtered to obtain 0.40 g of the title compound, mp 268°-271° dec.

Example 3

1-Cyclopropyl-7-(6,8-diazabicyclo[3.2.2]non-6-yl)-6-fluoro-1,4-dihydro-4-oxo-1,8-naphthyridine-3-carboxylic acid A solution of 1.41 g (5.0 mmol) of 7-chloro-1-cyclopropyl-6-fluoro-1,4-dihydro-4-oxo-1,8-naphthyridine-3-carboxylic acid, 1.10 (5.5 mmol) of 6,8-diazabicyclo[3.2.2]nonane, dihydrochloride, 2.26 ml (15 mmol) of 1,8-diazabicyclo[5.4.0]undec7-ene, and 30 ml of acetonitrile was heated under reflux for 4 hr. After cooling to room temperature, the precipitated solid was collected to give 0.97 g of the title compound, mp 255°-258° dec.

Example 4

1-Ethyl-6,8-difluoro-1,4-dihydro-7-(8-methyl-6,8-diazabicyclo[3.2.2]non-6-yl)-4-oxo-3-quinolinecarboxylic acid A mixture of 0.20 g (0.52 mmol) of 7-(6,8-diazabicyclo[3.2.2]non-6-yl)-1-ethyl-6,8-difluoro-1,4-dihydro-4-oxo-3-quinolinecarboxylic acid, 5 ml of 37% formaldehyde solution, and 5 ml of formic acid was heated under reflux for 3.6 hr. The reaction mixture was evaporated to dryness and the residue was suspended in ethanol/HCl. The solid was collected by filtration to give 0.16 g of the title compound as the hydrochloride salt, mp>300°.

Example 5

1-Cyclopropyl-7-[3-endo(ethylamino)-8-azabicyclo[3.2.1]oct-8-yl]-6-fluoro-1,4-dihydro-4-oxo-1,8-naphthyridine-3-carboxylic acid (5b)

A solution of 0.56 g (2.45 mmol) of 1-cyclopropyl-7-chloro-6-fluoro-1,4-dihydro-4-oxo-1,8-naphthyridine-3-carboxylic acid, 0.68 g (3.0 mmol) of 3-endo(ethylamino)-8-azabicyclo[3.2.1]octane, dihydrochloride, 0.90 ml (6.0 mmol) of 1,8-diazabicyclo[5.4.0]undec-7-ene, and 15 ml of acetonitrile was heated under reflux for 3 hr. The reaction mixture was cooled to room temperature and filtered and the solid was washed with ethanol to give 0.31 g of the title compound, mp 265°-268° C.

In the same manner the following compounds were prepared from 3-endo or -exo(ethylamino)-8-azabicyclo[3.2.1]octane, dihydrochloride and the appropriate quinoline or naphthyridine intermediate:

1-cyclopropyl-7-[3-exo(ethylamino)-8-azabicyclo[3.2.1]oct-8-yl]-6-fluoro-1,4-dihydro-4-oxo-1,8-naphthyridine-3-carboxylic acid, mp 236°-237° C.; (5a)

1-cyclopropyl-7-[3-endo(ethylamino)-8-azabicyclo[3.2.1]oct-8-yl]-6,8-difluoro-1,4-dihydro-4-oxo-3-quinolinecarboxylic acid, mp 242°-245° C. dec; (5c)

1-cyclopropyl-7-[3-exo(ethylamino)-8-azabicyclo[3.2.1]oct-8-yl]-6,8-difluoro-1,4-dihydro-4-oxo-3-quinolinecarboxylic acid, mp 233°-235° C.; (5d)

1-cyclopropyl-7-[3-endo(ethylamino)-8-azabicyclo[3.2.1]oct-8-yl]-6-fluoro-1,4-dihydro-4-oxo-3-quinolinecarboxylic acid, mp 276°-278° C. dec; (5f) and 1-cyclopropyl-7-[3-exo(ethylamino)-8-azabicyclo[3.2.1]oct-8-yl]-6-fluoro-1,4-dihydro-4-oxo-3-quinolinecarboxylic acid, mp 240°-242° C. dec (5e).

Example 6

7-(Azabicyclo[2.2.1]heptane)-6,8-difluoro-1-cyclopropyl-1,4-dihydro-4-oxo-quinoline-3-carboxylic acid 4.08 g (22 mmol) of 2-benzyl-2-azabicyclo[2.2.1]heptane-4-ene (S. D. Larsen and P. A. Grieco, *J. Amer. Chem. Soc.*, (1985), 107, 1768) was dissolved in 100 ml of methanol and to this solution was added 4.0 g of 20% methanolic hydrogen chloride and 1.0 g of 20% palladium on carbon. The reaction was pressurized with 50 psi of hydrogen gas and the flask shaken for 400 min. The reaction was purged of hydrogen then filtered through Celite and the Celite washed with methanol. The combined methanol filtrates were evaporated to a semisolid. This crude product was dissolved in 10 ml of hot isopropanol and cooled to −70° C. The crystals formed were collected by filtration and washed with cold (−70° C.) isopropanol and dried at 100 mmHg at 25° C. for 14 hr to give 0.95 g of 2-azabicyclo[2.2.1]heptane hydrochloride.

1.90 g (6.7 mmol) of 6,7,8-trifluoro-1-cyclopropyl-1,4-dihydro-4-oxo-quinoline-3-carboxylic acid, 0.9 g (6.7 mmol) of 2-azabicyclo[2.2.1]heptane hydrochloride, and 0.93 ml (6.7 mmol) of triethylamine were suspended in 40 ml of acetonitrile and the mixture refluxed for 52 hr. The reaction mixture was cooled to room temperature and the solid formed was collected by filtration. The solid was washed with acetonitrile and ethanol then dried at 30° C. at 100 mmHg overnight. This gave 1.67 g of the title compound; mp 278°–282° C. (dec).

Example 7

1-Cyclopropyl-7-(6,8-diazabicyclo[3.2.2]non-6-yl)-6-fluoro-1,4-dihydro-4-oxo-3-quinolinecarboxylic acid A solution of 0.53 g (2.0 mmol) of 1-cyclopropyl-6,7-difluoro-1,4-dihydro-4-oxo-3-quinolinecarboxylic acid, 0.44 g (2.2 mmol) of 6,8-diazabicyclo[3.2.2]nonane, dihydrochloride, 0.90 ml (6.0 mmol) of 1,8-diazabicyclo[5.4.0]undec-7-ene, and 10 ml of pyridine was heated under reflux for 4 hr. The reaction mixture was cooled to room temperature and the solid was filtered and washed with ethanol to yield 0.39 g of the title compound, mp 273°–276° dec.

Example 8

8-Chloro-1-cyclopropyl-7-(6,8-diazabicyclo[3.2.2]non-6-yl)-6-fluoro-1,4-dihydro-4-oxo-3-quinolinecarboxylic acid A suspension of 1.0 g (3.34 mmol) of 8-chloro-1-cyclopropyl-6,7-difluoro-1,4-dihydro-4-oxo-3-quinolinecarboxylic acid, 30 ml of acetonitrile, 1.52 g (10.0 mmol) of 1,8-diazabicyclo[5.4.0]undec7-ene, and 0.72 g (3.62 mmol) of 6,8-diazabicyclo [3.2.2]nonane, dihydrochloride was heated under reflux for 3 hr, then stirred at room temperature overnight. The precipitate was removed by filtration and washed with acetonitrile and ether to give 0.82 g of the title compound, mp 217°–220° C.

Example 9

5-Amino-1-cyclopropyl-7-(6,8-diazabicyclo[3.2.2]non-6-yl)-6,8-difluoro-1,4-dihydro-4-oxo-3-quinolinecarboxylic acid, hydrochloride A suspension of 4.5 g (15.0 mmol) of 5-amino-1-cyclopropyl-6,7,8-trifluoro-1,4-dihydro-4-oxo-3-quinolinecarboxylic acid, 180 ml of acetonitrile, 8.8 g (57.8 mmol) of 1,8-diazabicyclo[5.4.0]undec-7-ene, and 3.3 g (16.5 mmol) of 6,8-diazabicyclo[3.2.2]nonane was refluxed for 5 hr, then stirred at room temperature overnight. The precipitate was removed by filtration and washed with acetonitrile and ether. The crude product was dissolved in ethanol and treated with gaseous hydrogen chloride to give the hydrochloride, which was recrystallized from DMSO to give 2.3 g of the title compound, mp>300° C.

We claim:

1. A compound named 1-methyl-6,8-diazabicyclo [3.2.2]nonane.
2. A compound named 6-methyl-2,5-diazabicyclo [2,2,1]heptane.

* * * * *